United States Patent
Judell et al.

(10) Patent No.: US 7,184,928 B2
(45) Date of Patent: Feb. 27, 2007

(54) EXTENDED DEFECT SIZING

(75) Inventors: Neil Judell, Newtonville, MA (US); Michael Murphree, North Attleboro, MA (US)

(73) Assignee: ADE Corporation, Westwood, MA (US)

( * ) Notice: Subject to any disclaimer, the term of this patent is extended or adjusted under 35 U.S.C. 154(b) by 0 days.

(21) Appl. No.: 10/971,694

(22) Filed: Oct. 22, 2004

(65) Prior Publication Data

US 2005/0114091 A1    May 26, 2005

Related U.S. Application Data

(60) Provisional application No. 60/514,289, filed on Oct. 24, 2003.

(51) Int. Cl.
*G06F 101/14* (2006.01)
*G01F 15/00* (2006.01)
*G01F 17/18* (2006.01)

(52) U.S. Cl. ...................................... 702/179; 702/127
(58) Field of Classification Search ................ 702/179
See application file for complete search history.

(56) References Cited

U.S. PATENT DOCUMENTS

| 5,712,701 A | 1/1998 | Clementi et al. | 356/237 |
| 2003/0058455 A1* | 3/2003 | Ebihara et al. | 356/601 |

* cited by examiner

*Primary Examiner*—John Barlow
*Assistant Examiner*—Sujoy K. Kundu
(74) *Attorney, Agent, or Firm*—Weingarten, Schurgin, Gagnebin & Lebovici LLP (57) ABSTRACT

A system for inspecting semiconductor wafers capable of determining a scattering power associated with a wafer surface detect whether or not the scattering power exceeds the dynamic range of the system. The scattering power is obtained by determining the height of a Gaussian shape representing data collected by the system. The height is determined by defining a plurality of cross-sectional areas of the Gaussian shape, determining a value of each area, determining a value of the natural logarithm of intermediate heights of the Gaussian shape corresponding to the cross-sectional areas, plotting the area values as function of the natural logarithm of the intermediate height values to form a linear plot, determining a natural logarithm of the height value corresponding to a zero area value based on the linear plot, and determining the inverse natural logarithm of the value to obtain the height of the Gaussian shape.

4 Claims, 5 Drawing Sheets

EXTENDED DEFECT SIZING

CROSS REFERENCE TO RELATED APPLICATIONS

This application claims priority of U.S. Provisional Patent Application No. 60/514,289 filed Oct. 24, 2003 entitled EXTENDED DEFECT SIZING.

STATEMENT REGARDING FEDERALLY SPONSORED RESEARCH OR DEVELOPMENT

N/A

BACKGROUND OF THE INVENTION

The present application relates generally to systems and methods of inspecting semiconductor wafers, and more specifically to a semiconductor wafer inspection system and method capable of detecting and measuring wafer defects in which the scattering power of the defect exceeds the dynamic range of the system.

Systems and methods of inspecting semiconductor wafers are known for detecting and measuring defects occurring on a surface of a semiconductor wafer. For example, a conventional laser-based surface scanning inspection system is typically configured to detect localized light scatters on a semiconductor wafer surface. Such localized light scatters may be indicative of one or more defects in the wafer surface that may render an integrated circuit(s) (IC) fabricated on the wafer to be inoperative. In a typical mode of operation, the conventional surface scanning inspection system sweeps a laser light beam in a predetermined direction, while the wafer being inspected rotates under the swept beam at an angle of about 90° to the predetermined sweep direction. Next, the conventional surface scanning inspection system detects a light beam reflected from the wafer surface, and samples the detected signal in both the predetermined direction of the swept beam and in the direction of rotation to obtain a two-dimensional array of data. When the light beam sweeps over a defect in the wafer surface, the data obtained by the wafer inspection system generally corresponds to the beam shape of the laser spot power at the wafer surface. This is because such wafer surface defects are generally much smaller than the spot size of the laser beam. After the conventional surface scanning inspection system has detected a defect, the system may attempt to measure the size of the defect by determining the value of the maximum scattering power of the defect, and may also determine the location of the defect on the surface of the wafer.

One drawback of the above-described conventional laser-based surface scanning inspection system is that the maximum scattering power of a detected defect may exceed the dynamic range of the system. As a result, the electronics within the wafer inspection system may saturate, thereby causing at least some of the defect size measurements performed by the system to be at a power level at which the measurements become nonlinear due to the saturation effects.

One way of addressing the effects of saturation on defect size measurements made by the conventional laser-based surface scanning inspection system is to employ a data extrapolation technique. However, such data extrapolation techniques are often difficult to perform in conventional wafer inspection systems. Alternatively, the conventional surface scanning inspection system may perform a nonlinear least squares fit of the measurements to a given Gaussian shape, which may be characterized by a number of parameters including an estimated amplitude, an estimated inverse correlation matrix, and an estimated pulse center location. However, conventional algorithms for performing such nonlinear least squares fit techniques often require a significant amount of processing time. Further, relatively small changes in the data resulting from, e.g., noise or a non-ideal signal, may lead to significantly large changes in the estimated parameters.

It would therefore be desirable to have an improved system and method of inspecting semiconductor wafers that can measure the size and determine the location of a defect in a surface of a semiconductor wafer while avoiding the drawbacks of conventional wafer inspection systems and methods.

BRIEF SUMMARY OF THE INVENTION

In accordance with the present invention, a system and method of inspecting semiconductor wafers is provided that is capable of measuring the size and determining the location of a wafer surface defect whether or not the scattering power associated with the defect exceeds the dynamic range of the system.

In one embodiment, the semiconductor wafer inspection system includes an optical module including a surface scanning mechanism and a light channel (LC) detector including LC optics. In the preferred embodiment, the surface scanning mechanism is an acousto-optic deflector (AOD), and the LC optics comprises a quadcell photodetector. The AOD is configured to emit at least one collimated beam of laser light toward a surface of a semiconductor wafer at an oblique angle of incidence $\theta_i$, and the LC optics is configured to detect a light beam specularly reflected from the wafer surface at an angle of reflection $\theta_r$.

In the presently disclosed embodiment, the height of a defect detected on a semiconductor wafer surface using the surface scanning laser beam is obtained by determining the height of a Gaussian shape representing data collected by the wafer inspection system. In one embodiment, the height of a geometric Gaussian shape in three dimensional space is determined by defining a plurality of cross-sectional areas of the Gaussian shape, each cross-sectional area corresponding to a respective intermediate height of the Gaussian shape, determining a respective value of each defined cross-sectional area of the Gaussian shape, determining a respective value of the natural logarithm of each intermediate height of the Gaussian shape, determining a natural logarithm of the height value corresponding to a zero cross-sectional area value based on the substantially linear relationship between the natural logarithm of the intermediate heights and the cross-sectional areas, and determining the inverse natural logarithm of the value determined in the third determining step to obtain the height of the Gaussian shape. The disclosed method further includes determining a slope corresponding to the substantially linear relationship between the natural logarithm of the intermediate heights and the cross-sectional areas to obtain a 1/e area of the Gaussian shape.

In the preferred embodiment, the method of obtaining the height of a defect detected on a semiconductor wafer surface using the surface scanning laser beam includes plotting the determined cross-sectional area values as a function of the determined natural logarithm of the height values substantially in accordance with the equation $$\text{Area} = \pi |R|^{\frac{1}{2}} (\ln(P_0) - \ln(\text{height})),$$

in which "$P_0$" is a maximum scattering power associated with the detected defect, and "R" is a positive definite symmetric matrix describing a shape associated with the laser beam.

Other features, functions, and aspects of the invention will be evident from the Detailed Description of the Invention that follows.

BRIEF DESCRIPTION OF THE SEVERAL VIEWS OF THE DRAWINGS

The invention will be more fully understood with reference to the following Detailed Description of the Invention in conjunction with the drawings of which.

DETAILED DESCRIPTION OF THE INVENTION

U.S. Provisional Patent Application No. 60/514,289 filed Oct. 24, 2003 entitled EXTENDED DEFECT SIZING is incorporated herein by reference.

A system and method of inspecting a semiconductor wafer is disclosed that is capable of measuring the size and determining the location of a defect on a surface of a semiconductor wafer. The presently disclosed wafer inspection system can perform such sizing and locating of wafer surface defects whether or not the scattering power associated with the defect exceeds the dynamic range of the system.

Figure 1:
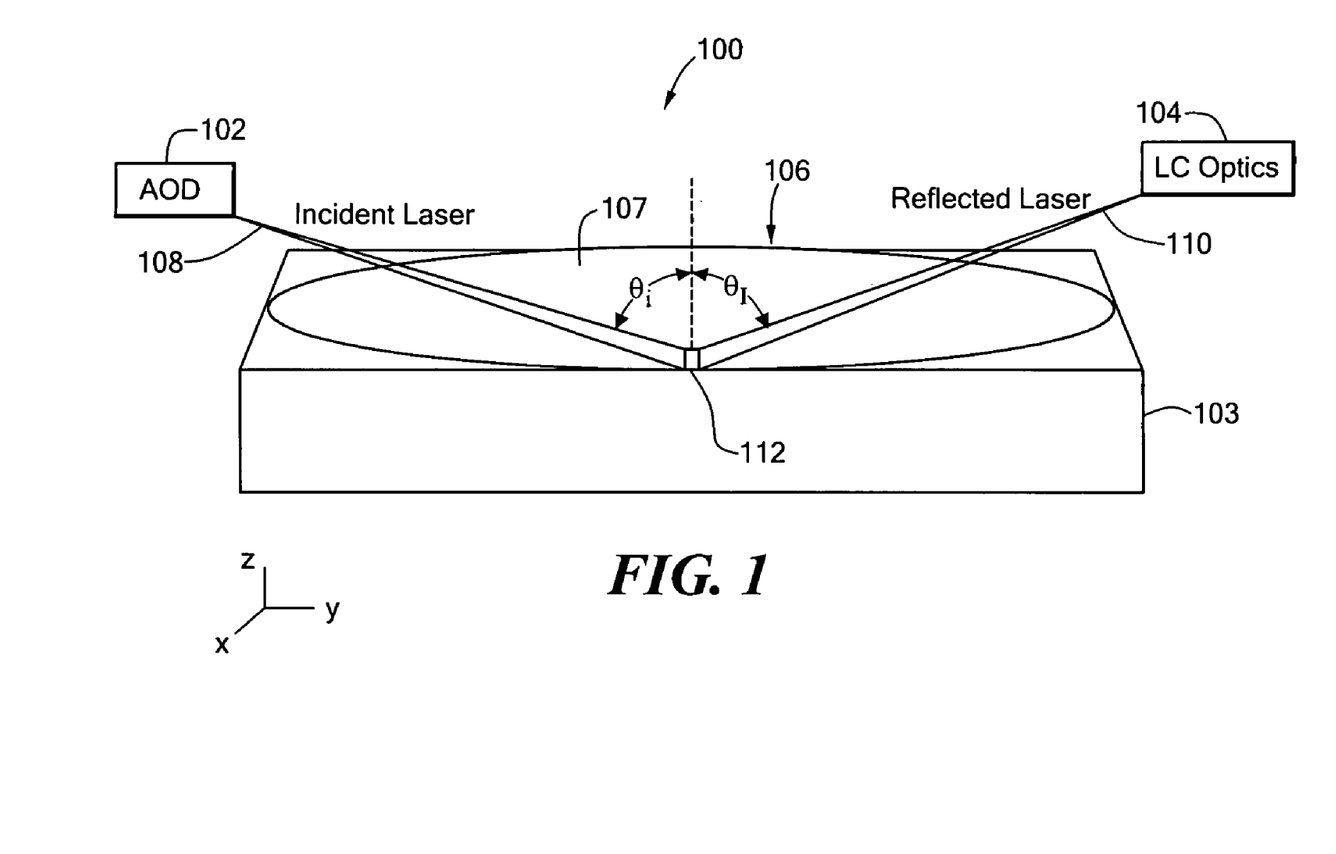
FIG. 1 is a block diagram of a laser-based wafer surface scanning inspection system according to the present invention, in which the system performs a scan of a laser beam on a surface of a semiconductor wafer to detect defects in the wafer surface.

FIG. 1 depicts an illustrative embodiment of a laser-based wafer surface scanning inspection system 100, in accordance with the present invention. In the illustrated embodiment, the surface scanning inspection system 100 comprises an optical module including a surface scanning mechanism 102, and a light channel (LC) detector including LC optics 104. For example, the surface scanning mechanism 102 may be an acousto-optic deflector (AOD) or any other suitable surface scanning mechanism, and the LC optics 102 may comprise a quadcell photodetector or any other suitable light detector. As shown in FIG. 1, the AOD 102 is configured to emit at least one collimated beam of laser light 108 toward a surface 107 of a semiconductor wafer 106 at an oblique angle of incidence $\theta_i$. Further, the LC optics 104 is configured to detect a light beam 110 specularly reflected from the wafer surface 107 at an angle of reflection $\theta_r$. Specifically, the LC optics 104 is configured to detect specular distortions in the reflected light beam 110. It is noted that the wafer 106 may also be inspected from the backside by inverting the wafer in the surface scanning inspection system 100.

For example, the AOD 102 may include a solid state laser such as a 532 nm wavelength diode-pulsed solid state laser, or any other suitable type of laser. In the preferred embodiment, the AOD 102 emits the laser light beam 108 to produce a focused laser spot having a diameter of about 30 microns for scanning the wafer surface 107, in which the incident angle θi of the emitted light beam 108 is about 65 degrees. It should be understood that the laser light beam 108 may alternatively be emitted by the AOD 102 at any suitable angle of incidence to produce any suitable spot size on the wafer surface. The surface scanning inspection system 100 further includes a theta stage 103 upon which the wafer 106 is held during inspection. The theta stage 103 is configured to rotate and to translate the wafer 106 through a scan line 112 produced by the AOD 102, thereby generating a spiral pattern of light used to inspect the wafer surface 107. The theta stage 103 includes an encoder such as an optical encoder that provides counts indicative of the rotational position of the stage 103 relative to a predetermined reference point. It is noted that the structure and operation of the theta stage 103 are known to those skilled in this art and therefore need not be described in detail herein.

Figure 2:
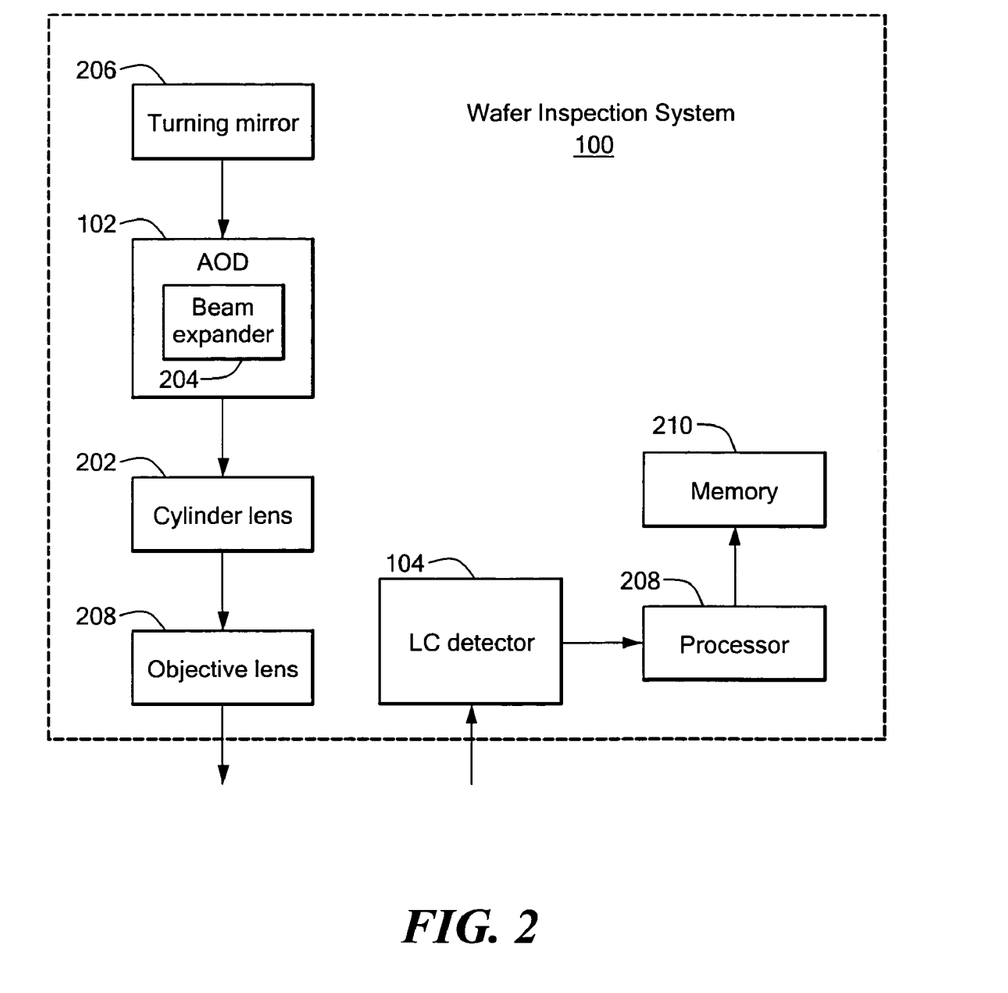
FIG. 2 is a functional illustration of components included in the surface scanning inspection system of FIG. 1.

FIG. 2 depicts a plurality of functional components included in the above-described surface scanning inspection system 100 (see FIG. 1). As shown in FIG. 2, the surface scanning inspection system 100 comprises a turning mirror 206, the AOD 102 including a beam expander 204, a cylinder lens 202, an objective lens 208, the LC optics 104, and a processor 208 and associated memory 210. In the illustrated embodiment, the AOD 102 is configured to generate the narrow angle light beam 108 by exciting a crystal with a high frequency sound wave. The beam expander 204 is configured to expand the light beam 108 before the beam enters an aperture of the AOD 102 to obtain a desired angle of deflection. The cylinder lens 202 is disposed at the output of the AOD 102, and is configured to compensate for parasitic cylinder lens loss that may be induced by the deflector. The scan is relayed through the objective lens 208 to the surface 107 of the wafer 106 (see also FIG. 1). The LC optics 104 is configured to receive the reflected light beam 110, and to detect any losses in light intensity resulting from specular distortion or deflection of the light beam 110.

In the preferred mode of operation, the surface scanning inspection system 100 (see FIG. 1) is configured to detect localized light scatters on the surface 107 of the wafer 106. For example, such localized light scatters may be indicative of one or more defects in the wafer surface 107 that may render an integrated circuit(s) (IC) fabricated on the wafer 106 to be inoperative. Specifically, the AOD 102 emits the laser light beam 108 toward the wafer surface 107 at the angle of incidence $\theta_i$ and sweeps the light beam 108 in a predetermined radial direction, while the theta stage 103 rotates under the swept beam 108 at an angle of about 90° to the predetermined radial direction. Next, the LC optics 104 detects the laser light beam 110 reflected from the wafer surface 107 at the angle of reflection $\theta_r$, and samples the detected signal in both the radial and rotational directions to obtain a two-dimensional array of data. It is noted that the sampling of the data is generally non-orthogonal. The processor 208 included in the surface scanning inspection system 100 is operative to process the sampled data by executing one or more programs out of its associated memory 210 (see FIG. 2).

In the presently disclosed embodiment, the corresponding location of each data sample on the wafer surface 107 is expressed as $$x_{in,xs}, y_{in,xs}, \tag{1}$$

in which the index "in" designates samples in the radial or "in scan" direction, and the index "xs" designates samples in the tangential or "cross scan" direction.

When the light beam 108 sweeps over a defect in the wafer surface 107, the data samples obtained by the surface scanning inspection system 100 generally correspond to the beam shape of the laser spot on the surface 107. This is because wafer surface defects are normally much smaller than the spot size of the laser beam 108. For example, the data samples may be represented by a geometric Gaussian shape that is non-isotropic due to the angle of incidence $\theta i$ and the non-orthogonal sampling of the data.

The locations $(x_{in,xs}, y_{in,xs})$ of the data samples on the wafer surface 107 may be expressed as a column vector, i.e., $$\vec{z} = \begin{bmatrix} x_{in,xs} \\ y_{in,xs} \end{bmatrix}. \tag{2}$$

Accordingly, the optical laser spot power at the wafer surface 107 may be expressed as $$\text{power}(\vec{z}) = P_0 \exp(-(\vec{z} - \vec{z}_0)^t R^{-1} (\vec{z} - \vec{z}_0)), \tag{3}$$

in which "$P_0$" is the maximum scattering power of the defect, "$\vec{z}_0$" denotes the location of the defect, and "R" is a positive definite symmetric matrix describing the beam shape.

For example, if a laser spot is a Gaussian with a density of $\text{density}(x) = e^{-x^2/2\sigma^2}$, then the $1/e^2$ full-width may be expressed as $4\sigma$. For an illustrative 50 micron $1/e^2$ full-width beam, which strikes a wafer at a 65 degree incident angle, then the density at the wafer surface may be expressed as $$\text{density}(x, y) = e^{-x^2/2(12.5\mu)^2} e^{-y^2/2(12.5\mu/\cos(65°))^2}. \tag{4}$$

Equation (4) above may be rewritten as $$\text{density}(x, y) = \exp\left(\begin{bmatrix} x \\ y \end{bmatrix}^t \begin{bmatrix} (12.5\mu)^2 & 0 \\ 0 & (12.5\mu/\cos(65°))^2 \end{bmatrix}^{-1} \begin{bmatrix} x \\ y \end{bmatrix}\right). \tag{5}$$

Accordingly, for this illustrative example, $$R = \begin{bmatrix} (12.5\mu)^2 & 0 \\ 0 & (12.5\mu/\cos(65°))^2 \end{bmatrix}. \tag{6}$$

In the event the sampled data comprises non-saturated data (i.e., the data sampling is linear), the surface scanning inspection system 100 may determine the value of $P_0$ in equation (3) above by identifying the largest value in the collection of measured data points, which may be expressed as $$\text{power}(x_{in,xs}, y_{in,xs}). \tag{7}$$

However, this technique for determining the value of $P_0$ generally does not yield useful results when the maximum scattering power of a detected defect exceeds the dynamic range of the surface scanning inspection system 100, i.e., when the sampled data comprises saturated data. As a result, at least some of the defect size measurements performed by the wafer inspection system may be at a power level at which the measurements become nonlinear due to the saturation effects.

According to the present invention, a technique is provided for measuring the size and determining the location of a defect on a surface of a semiconductor wafer when the maximum scattering power of a detected defect exceeds the dynamic range of the surface scanning inspection system 100, i.e., the sampled data collected by the wafer inspection system comprises saturated data. It is noted that the disclosed technique may be employed in the voltage domain for sizing wafer defects.

Figure 3:
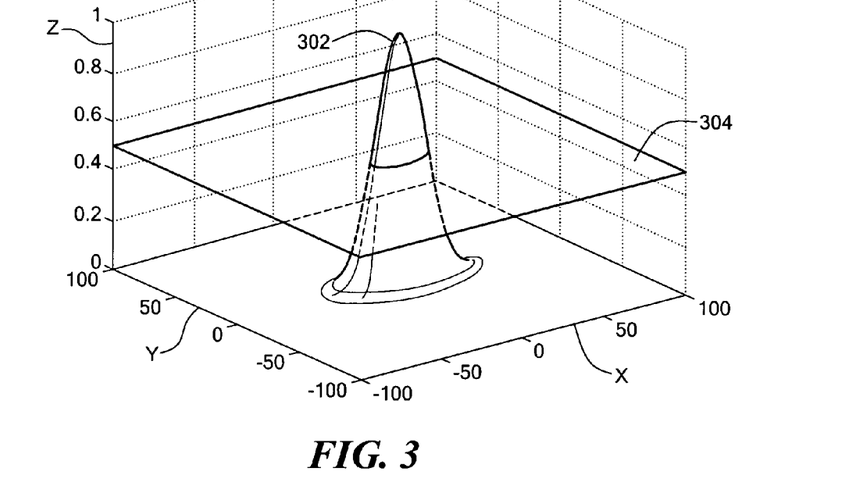
FIG. 3 is a diagram of a first geometric Gaussian shape in three-dimensional space, the first Gaussian shape representing non-saturated data collected by the surface scanning inspection system of FIG. 1.
Figure 4:
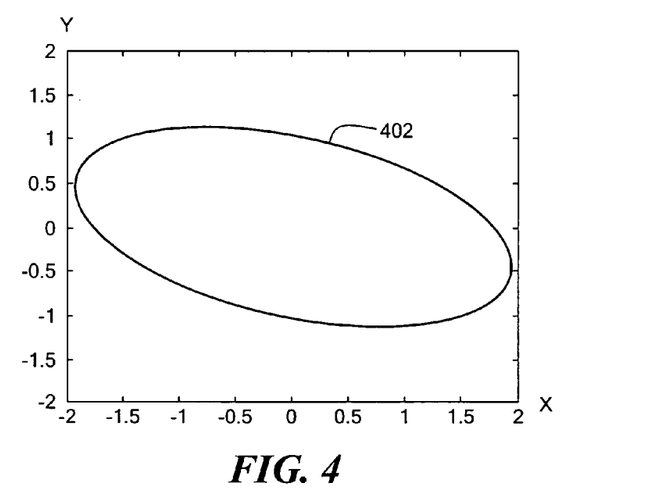
FIG. 4 is a diagram of an elliptical cross-sectional area of the first Gaussian shape of FIG. 3, the cross-sectional area being obtained by conceptually cutting the first Gaussian shape in an x-y plane corresponding to a predetermined height of the Gaussian shape.

The presently disclosed technique will be better understood by reference to the following analysis. FIG. 3 depicts a geometric Gaussian shape 302 in a space defined by x, y, and z axes, in which the Gaussian shape 302 represents non-saturated data collected by the surface scanning inspection system 100 (see FIG. 1). If the Gaussian shape 302 is conceptually cut by an x-y plane 304 at a predetermined amplitude ("cut height") along the z-axis, then the resulting cross-sectional area of the Gaussian shape 302 in the x-y plane 304 has the shape of an ellipse 402 (see FIG. 4). The area of the ellipse 402 may be determined by solving for the area of a region defined by $$\text{power}(\vec{z}) > \text{height}, \tag{8}$$

in which "$\text{power}(\vec{z})$" is expressed as indicated in equation (3) above. Substituting this expression for $\text{power}(\vec{z})$ in equation (8) yields $$(\vec{z} - \vec{z}_0)^t R^{-1} (\vec{z} - \vec{z}_0) < \ln(P_0) - \ln(\text{height}). \tag{9}$$

Let $$\text{Area} = \int\int_{(\vec{z}-\vec{z}_0)^t R^{-1}(\vec{z}-\vec{z}_0) < \ln(P_0)-\ln(height)} dz, \tag{10}$$

and $$y = R^{-\frac{1}{2}}(\vec{z} - \vec{z}_0), \tag{11}$$

$$dy = |R|^{-\frac{1}{2}} dz,$$

$$dz = |R|^{\frac{1}{2}} dy.$$

Accordingly, $$\text{Area} = \int\int_{|y| < \sqrt{\ln(P_0)-\ln(height)}} |R|^{\frac{1}{2}} dy, \tag{12}$$

$$\text{Area} = \int_0^{2\pi} \int^{\sqrt{\ln(P_0)-\ln(height)}} |R|^{\frac{1}{2}} r \, dr \, d\theta, \text{ and} \tag{13}$$

$$\text{Area} = \pi |R|^{\frac{1}{2}} (\ln(P_0) - \ln(\text{height})). \tag{14}$$

Equation (14) above shows that the area of a geometric Gaussian shape conceptually cut at a predetermined height (e.g., the area of the ellipse 402; see FIG. 4) is a linear function of the natural logarithm (ln) of the predetermined cut height. As indicated by equation (14), the cross-sectional area is equal to zero when the cut height equals the scattering power $P_0$ of the defect. Further, the slope of the line defined by equation (14) is equal to $$\pi |R|^{1/2}, \quad (15)$$

in which "$|R|^{1/2}$" is the square root of the determinant of the positive definite symmetric matrix describing the beam shape. It is noted that "$\pi |R|^{1/2}$" is equal to the "1/e" area of the Gaussian shape. Accordingly, after plotting the area values as a function of the natural logarithm (ln) of the predetermined cut heights, and applying a least squares fit to the plot to form a linear plot, the intercept at which the area is zero is equal to the natural logarithm of the scattering power $P_0$, and the slope of the linear plot is equal to the 1/e area of the Gaussian shape.

Figure 5:
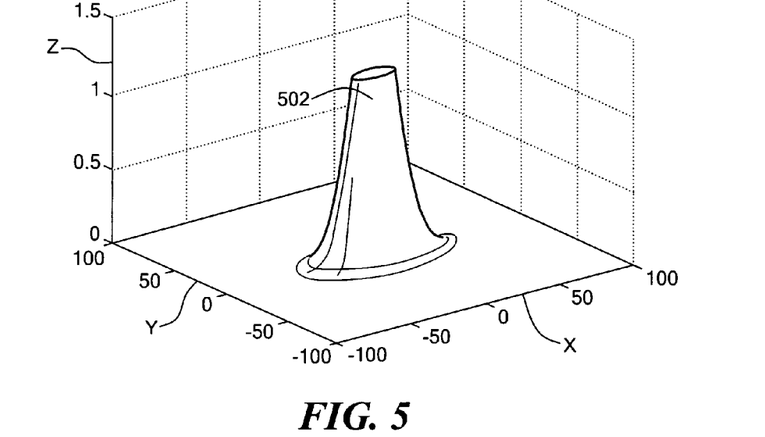
FIG. 5 is a diagram of a second geometric Gaussian shape in three-dimensional space, the second Gaussian shape representing saturated data collected by the surface scanning inspection system of FIG. 1.
Figure 6:
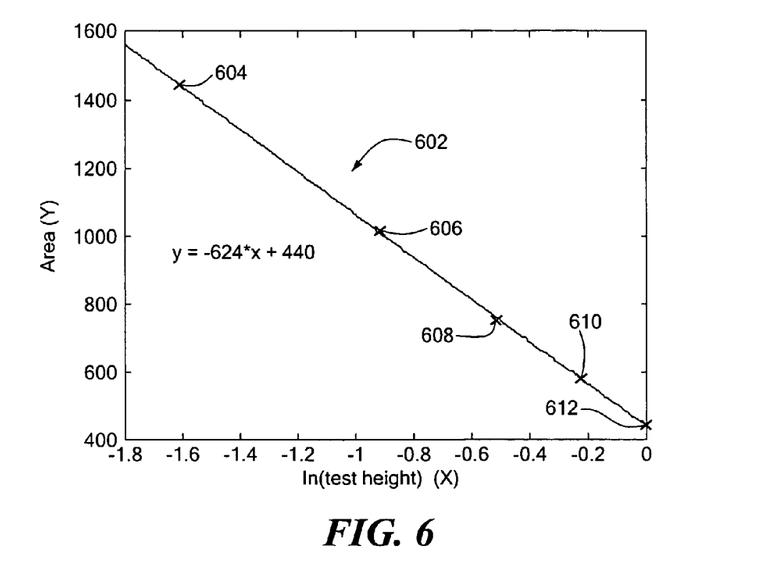
FIG. 6 is a diagram illustrating a linear least squares fit of the data represented by the second Gaussian shape of FIG. 5.

The presently disclosed technique for measuring the size and determining the location of a defect on a semiconductor wafer surface is illustrated by the following example. FIG. 5 depicts a geometric Gaussian shape 502 in x, y, z coordinate space, in which the Gaussian shape 502 comprises saturated data collected by the surface scanning inspection system 100 (see FIG. 1). In this example, the Gaussian shape 502 is conceptually cut in the x-y plane at a plurality of predetermined cut heights along the z-axis, namely, at cut heights of 0.2, 0.4, 0.6, 0.8, and 1.0 units. Next, the respective cross-sectional areas of the Gaussian shape 502 conceptually cut at these predetermined heights are determined. The values of the cross-sectional areas are then plotted versus the natural logarithm (ln) of the respective cut heights, and a least squares fit is applied to the plot to produce a linear plot 602 of the collected data, as depicted in FIG. 6. As shown in FIG. 6, the linear plot 602 includes the data points 604, 606, 608, 610, and 612 corresponding to the predetermined cut heights 0.2, 0.4, 0.6, 0.8, and 1.0, respectively. In this illustrative example, the linear plot 602 may be expressed as $$y = -624x + 440, \quad (16)$$

in which the variable "y" represents the cross-sectional area of the Gaussian shape 502 and the variable "x" represents the natural logarithm of the predetermined cut height.

Accordingly, equation (16) above indicates that the cross-sectional area (y) is equal to zero when the natural logarithm of the cut height (x) equals about 0.705. The cut height at which the cross-sectional area equals zero may therefore be obtained by taking the inverse natural logarithm of 0.705, which is about 2.02. Because the cross-sectional area is equal to zero when the cut height equals the scattering power $P_0$ of a wafer surface defect, as indicated in equation (14) above, $P_0$ is equal to about 2.02. In this example, the actual height of the illustrative Gaussian shape 502 (i.e., the height that would be observed in the absence of saturation effects) is 2.0. Further, the slope of the linear plot 602, as expressed by equation (16) above, is equal to -624, which is the 1/e area of the Gaussian shape. In this example, the actual 1/e area of the Gaussian shape 502 (i.e., the 1/e area that would be observed in the absence of saturation effects) is $200\pi$, or about 628. Based on these results, a correlation coefficient may be calculated as 0.9999. In general, if the correlation coefficient is much less than unity, then the linear least squares fit is considered to be poor. Because the correlation coefficient is equal to 0.9999 in this illustrative example, the linear least squares fit is consider to provide an accurate measure of the actual height of the Gaussian shape 502.

Figure 7:
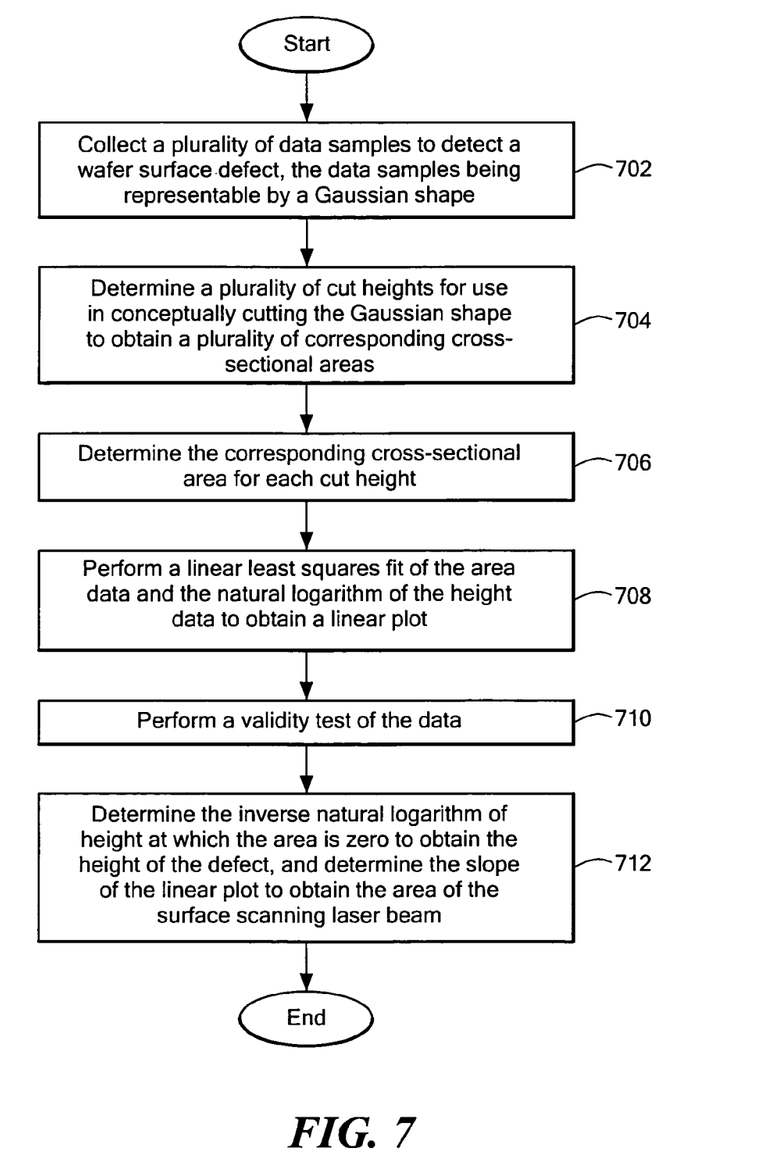
FIG. 7 is a flow diagram of a method of operating the surface scanning inspection system of FIG. 1.

A method of operating the presently disclosed surface scanning inspection system to determine the amplitude (height) and the 1/e area of a Gaussian shape is illustrated with reference to FIG. 7. It is understood that the height of the Gaussian shape corresponds to the height of a defect detected on a semiconductor wafer surface, and the 1/e area of the Gaussian shape corresponds to the area of a surface scanning laser beam emitted by the wafer inspection system. As depicted in step 702, the wafer inspection system collects a plurality of data samples and analyzes the data samples to detect a defect in the semiconductor wafer surface. It is noted that the data samples, which may comprise saturated data, may be diagrammatically represented by a geometric Gaussian shape. Next, a plurality of predetermined cut heights is determined, as depicted in step 704, for use in conceptually cutting the Gaussian shape to obtain a plurality of corresponding cross-sectional areas of the Gaussian shape. In the preferred embodiment, the plurality of predetermined cut heights includes about 10 height values, ranging from about 20% to about 80% of the maximum height of the Gaussian shape, as indicated by the collected data samples. Relatively small cut height values are preferably omitted to avoid noise effects. For each predetermined cut height, the corresponding cross-sectional area of the Gaussian shape is determined, as depicted in step 706. In the preferred embodiment, the cross-sectional areas are determined by counting the number of data values that exceed the predetermined cut height, and then multiplying the counted number of data values by the effective area of each value. For example, a useful approximation of the effective cross-sectional area may be obtained by calculating the product of (1) the radial in scan pixel pitch, (2) the tangential cross scan pixel pitch, and (3) the cosine of the boom tilt, which is defined as $\pi/2$ radians minus the angle between the in scan and cross scan directions. Next, a linear least squares fit of the data is performed, as depicted in step 708, to obtain a linear plot of the data. For example, in a mathematical expression of the linear plot, the variable "x" corresponds to the natural logarithm (ln) of the predetermined cut heights, and the variable "y" corresponds to the determined cross-sectional areas of the Gaussian shape (e.g., see equation (16)). A validity test of the regression is then performed, as depicted in step 710, to generate correlation coefficient. If the correlation coefficient value is close to unity, then the above-described method may be employed to provide an accurate measure of the height of the detected defect. Finally, the inverse natural logarithm of the cut height at which the cross-sectional area is zero is determined, as depicted in step 712, to obtain the height of the detected defect, and the slope of the linear plot is determined, as also depicted in step 712, to obtain the area of the surface scanning laser beam. It is noted that the determined area of the surface scanning laser beam may be employed by the wafer inspection system as a diagnostic measure.

Having described the above illustrative embodiments, other alternative embodiments or variations may be made. For example, it was described that a linear least squares fit may be employed for fitting the cross-sectional areas to the natural logarithms of the predetermined cut heights. However, such linear least squares fitting was described for purposes of illustration, and other techniques may be employed, including a polynomial fit, a nonlinear least squares fit, or a noise weighted least squares fit technique.

It will be appreciated by those of ordinary skill in the art that further modifications to and variations of the above-described extended defect sizing technique may be made without departing from the inventive concepts disclosed herein. Accordingly, the invention should not be viewed as limited except as by the scope and spirit of the appended claims.

What is claimed is:

1. In a semiconductor wafer inspection system, a method of determining a size of a defect on a semiconductor wafer surface, said method being performable by a processor executing at least one program out of a memory for processing data samples corresponding to said wafer surface defect, said data samples being represented by a geometric Gaussian shape in three dimensional space, said method comprising the steps of:

defining a plurality of cross-sectional areas of the Gaussian shape, each cross-sectional area corresponding to a respective intermediate height of the Gaussian shape;

in a first determining step, determining a respective value of each defined cross-sectional area of the Gaussian shape;

in a second determining step, determining a respective value of the natural logarithm of each intermediate height of the Gaussian shape;

in a third determining step, determining a natural logarithm of the height value corresponding to a zero cross-sectional area value based on a substantially linear function of the cross-sectional area values versus the natural logarithm of the intermediate height values;

in a fourth determining step, determining the inverse natural logarithm of the value determined in the third determining step to obtain a value of a full height of the Gaussian shape, wherein the value of the full height of the Gaussian shape corresponds to a value of the size of said wafer surface defect detected on a semiconductor wafer surface using a surface scanning laser beam; and storing said value of the size of said wafer surface defect in said memory.

2. The method of claim 1 further including the step of determining a slope of the substantially linear function to obtain a 1/e area of the Gaussian shape.

3. The method of claim 1 further including the steps of applying at least one of a linear least squares fit technique, a polynomial fit technique, a nonlinear least squares fit technique, or a noise weighted least squares fit technique to the substantially linear function of the cross-sectional area values to form a linear function.

4. The method of claim 1 further including the step of determining the cross-sectional area values as a function of the natural logarithm of the intermediate height values to form a substantially linear function, and wherein the step of determining the cross-sectional area values as a function of the natural logarithm of the height values is performed substantially in accordance with the equation $$\text{Area} = \pi |R|^{1/2} (ln(P_0) - ln(\text{height}))$$

wherein "$P_0$" is a maximum scattering power associated with the detected defect, and "$R$" is a positive definite symmetric matrix describing a shape associated with the laser beam.

* * * * *

UNITED STATES PATENT AND TRADEMARK OFFICE
CERTIFICATE OF CORRECTION

PATENT NO.        : 7,184,928 B2  
APPLICATION NO.   : 10/971694  
DATED             : February 27, 2007  
INVENTOR(S)       : Neil Judell et al.

Page 1 of 1

It is certified that error appears in the above-identified patent and that said Letters Patent is hereby corrected as shown below:

Column 5, Line eq. 1, $^x$in, xs, yin, xs, should read --$^x$in, xs, Yin, xs--;

Column 8, Line 43, "(in)" should read --(1n)--.

Signed and Sealed this

Fifth Day of August, 2008

JON W. DUDAS  
*Director of the United States Patent and Trademark Office*